(12) United States Patent
Jin

(10) Patent No.: US 11,666,671 B2
(45) Date of Patent: Jun. 6, 2023

(54) SPATIAL MAPPING OF KIDNEY FUNCTIONS

(71) Applicant: Northwestern University, Evanston, IL (US)

(72) Inventor: Jing Jin, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/059,606

(22) PCT Filed: May 31, 2019

(86) PCT No.: PCT/US2019/034973
§ 371 (c)(1),
(2) Date: Nov. 30, 2020

(87) PCT Pub. No.: WO2019/232418
PCT Pub. Date: Dec. 5, 2019

(65) Prior Publication Data
US 2021/0205484 A1 Jul. 8, 2021

Related U.S. Application Data

(60) Provisional application No. 62/679,484, filed on Jun. 1, 2018.

(51) Int. Cl.
*A61K 51/08* (2006.01)
*A61K 51/10* (2006.01)

(52) U.S. Cl.
CPC ............ *A61K 51/088* (2013.01); *A61K 51/10* (2013.01)

(58) Field of Classification Search
CPC ...... A61K 51/00; A61K 51/08; A61K 51/088; A61K 51/10

USPC ...... 424/1.11, 1.49, 1.65, 1.69, 9.1, 9.4, 9.2, 424/9.3; 534/7, 10–14; 530/300; 514/1, 514/1.1
See application file for complete search history.

(56) References Cited

U.S. PATENT DOCUMENTS

| | | | |
|---|---|---|---|
| 9,745,350 B2 * | 8/2017 | Malm | A61P 35/00 |
| 2013/0330274 A1 | 12/2013 | Berr et al. | |
| 2015/0157747 A1 | 6/2015 | Miao et al. | |
| 2015/0374862 A1 | 12/2015 | Kelly | |
| 2016/0151515 A1 | 6/2016 | Joubert et al. | |

FOREIGN PATENT DOCUMENTS

WO 2007019376 A1 2/2007

OTHER PUBLICATIONS

International Search Report and Written Opinion issued in PCT application PCT/US2019/034973, dated Oct. 1, 2019.
International Preliminary Report on Patentability issued in PCT application PCT/US2019/034973, dated Dec. 1, 2020.

* cited by examiner

*Primary Examiner* — D. L. Jones
(74) *Attorney, Agent, or Firm* — Benesch, Friedlander, Coplan & Aronoff LLP

(57) ABSTRACT

A molecular imaging agent including a detectable moiety, a chelation moiety, and a carrier moiety is provided. In one embodiment, the detectable moiety is coupled to the chelation moiety and the chelation moiety is linked to the carrier moiety. In another embodiment, the detectable moiety is $^{99m}$Tc; the chelation moiety includes HYNIC; and the carrier moiety includes from N-terminus to C-terminus: a His6 purification tag, a human VEGFA polybasic tag sequence, and a human Fc stabilization segment.

12 Claims, 10 Drawing Sheets
Specification includes a Sequence Listing.

SPATIAL MAPPING OF KIDNEY FUNCTIONS

RELATED APPLICATIONS

This application is the national phase entry of PCT/US19/34973 filed May 31, 2019, which claims priority to U.S. Provisional Patent Application No. 62/679,484, filed on Jun. 1, 2018, entitled "Spatial Mapping of Kidney Filtration," which is incorporated herein in its entirety.

REFERENCE TO A SEQUENCE LISTING

The instant application contains a Sequence Listing which has been filed electronically in ASCII format and is hereby incorporated by reference in its entirety. Said ASCII copy, created on 30 Nov. 2020 is named 47460_115_ST25.txt and is 6,096 bytes in size.

FIELD

Provided herein are protein carrier-based probes for renal scanning using nuclear medicine imaging.

BACKGROUND

In nephrology clinic, renal scan using radionuclide-bound tracers is prescribed to patients for evaluating their kidney functions, as well as for detecting structural or morphological abnormalities. The most commonly used tracers, such as DTPA, MAG3, DMSA, among others, are chemical compounds that chelate radionuclides, such as Technitium-99m ($^{99m}$Tc), and others. These small molecule radionuclide-bound tracers, once injected to blood circulation, follow the path of renal clearance by the combination of kidney glomerular filtration, renal tubular secretion, and urinary excretion and through other routes. Due to the lack of specific retention in the renal tissues, these tracers are considered "passive" contrast enhancement agents. Generally, the dynamic radio image of the kidney at a given time reflects the net content of the radionuclide, for example $^{99m}$Tc, by the kidney as the result of these concurrent processes.

Due to the lack of target fixation of radionuclide in the kidney, the radio signal pattern in the kidney constantly changes, which makes it technically challenging to perform signal acquisition for an extended time period without compromising on image sharpness or resolution. Consequently, during a short timeframe, (typically 15-30 seconds per frame of signal acquisition), 2-dimensional renal scintigraphy or single-photon emission computerized tomography (SPECT) for example, can only collect a limited amount of radio signal with low-resolution images.

It would be beneficial to develop a molecular imaging agent that specifically targets renal structures with better renal retention. This will significantly improve signal-to-noise ratios (renal vs. non-renal tissues). When used in conjunction with existing nuclear medicine imaging technology, the targeted tracer will greatly improve renogram image resolution. Furthermore, targeted tracers from our purposed design can be more informative in revealing the kidney parenchyma that is affected by the disease.

SUMMARY

A molecular imaging agent including a detectable moiety, a chelation moiety, and a carrier moiety is provided. In one embodiment, the detectable moiety is coupled to the chelation moiety and the chelation moiety is linked to the carrier moiety. In another embodiment, the detectable moiety is $^{99m}$Tc; the chelation moiety includes HYNIC; and the carrier moiety includes from N-terminus to C-terminus: a His$_6$ purification tag, a human VEGFA polybasic sequence, and a human Fc stabilization segment.

In some embodiments, upon administration of the molecular imaging agent to a subject through intravenous injection, the molecular imaging agent is cleared from the blood by the kidneys. In other embodiments, the molecular imaging agent collects in the kidney, without significant clearance into the bladder. In yet other embodiments, less than 25% (e.g., 20%, 15%, 10%, 5%, 2%, 1%, 0.5%, 0.2%, 0.1%, or less, or ranges therebetween (e.g., 0.5% or less)) of the molecular imaging agent in the kidney is cleared to the bladder in a time period of one day or less (e.g., 1 day, 12 hours, 6 hours, 2 hours, 1 hour, 30 minutes, 20 minutes, 10 minutes, 5 minutes, 1 minute, or less, or ranges therebetween). In some embodiments, the molecular imaging agent becomes fixed at the basement membrane of renal tubules.

In one embodiment, the detectable moiety is $^{99m}$Tc. In some embodiments, the chelation moiety includes 6-hydrazinopyridine-3-carboxylic acid (HYNIC). In some embodiments, the carrier moiety includes a purification tag, a polybasic tag (PBT) sequence, and/or a stabilization segment. In some embodiments, the purification tag is a His$_6$ tag (SEQ ID NO: 3). In some embodiments, the polybasic sequence includes at least 70% (e.g., 70%, 75%, 80%, 85%, 90%, 95%, or more or ranges therebetween) sequence identity with SEQ ID NO: 1 (e.g., over the entire length of SEQ ID NO: 1). In some embodiments, the polybasic tag (PBT) sequence includes at least 70% (e.g., 70%, 75%, 80%, 85%, 90%, 95%, or more or ranges therebetween) sequence similarity with SEQ ID NO: 3 (e.g., over the entire length of SEQ ID NO: 3). In some embodiments, the stabilization segment includes at least 70% (e.g., 70%, 75%, 80%, 85%, 90%, 95%, or more or ranges therebetween) sequence identity with all or a portion of human IgG1 Fc. In some embodiments, the stabilization segment includes at least 70% (e.g., 70%, 75%, 80%, 85%, 90%, 95%, or more or ranges therebetween) sequence similarity with all or a portion of human IgG1 Fc. In some embodiments, wherein the detectable moiety is $^{99m}$Tc; the chelation moiety includes HYNIC; and the carrier moiety includes, from N-terminus to C-terminus: a His$_6$ purification tag, a human VEGFA polybasic sequence, and a human IgG1 Fc stabilization segment.

In some embodiments, provided herein are methods of assessing and/or monitoring a kidney of a subject including administering to the subject a molecular imaging agent and performing a renal scan of the subject. In some embodiments, the renal scan includes 2-dimensional scintigraphy, positron emission tomography (PET) or SPECT. In some embodiments, methods further include diagnosing the subject with a kidney disease, injury or condition.

BRIEF DESCRIPTION OF THE SEQUENCES

SEQ ID NO: 1 is a Polybasic tag (PBT) derived from human VEGFA, protein sequence accession: NP_001020537.2. The PBT may be amino acids 131-163 of human VEGFA. The encoding VEGFA transcript of protein accession no: NP_001020537 has been reported to have two translational starting sites. One is the conventional ATG/AUG start; the other is an alternative translational start site using an unconventional start codon of "CTG/CUG", which produces a longer variant of VEGFA protein with an extra 180 amino acid sequence extended from the amino-terminal of the starting methionine (M) encoded by the conventional "ATG" start codon. If this 180 extension is considered part of the full length VEGFA sequence, the PBT segment comprises from amino acids: 311-343. SEQ ID NO: 1 has the following amino acid sequence:

```
            SEQ ID NO: 1:
                                          (SEQ ID NO: 1)
    RPKKDRARQEKKSVRGKGKGQKRKRKKSRYKSW
```

SEQ ID NO: 2 is the fragment crystallizable region (Fc region) derived from human IgG1/IGHG1. SEQ ID NO: 2 comprises amino acids 239-470 of a representative protein sequence accession: AIC63046, encoded by KJ905795.1 transcript. The protein segment has the following sequence:

```
SEQ ID NO: 2:
                                          (SEQ ID NO: 2)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

SEQ ID NO: 3 is a poly-Histidine (6×His affinity tag) sequence derived from pET-30a(+) vector by Novagen (EMD Millipore). The polypeptide tag has the following sequence:

```
            SEQ ID NO: 3:
                                          (SEQ ID NO: 3)
                HHHHHH_
```

SEQ ID NO: 4: is an exemplary full amino acid sequence of the PBT-Fc probe used for SPECT imaging including the 6×His, PBT and Fc segments in an amino terminus to carboxyl terminus order, and additional linkers (encoded by pET30a(+) vector) in between. The PBT-Fc probe has the following sequence:

```
SEQ ID NO: 4:
                                          (SEQ ID NO: 4)
MHHHHHHSSGLVPRGSGMKETAAAKFERQHMDSPDLGTDDDDKAMADIGS

EFRPKKDRARQEKKSVRGKGKGQKRKRKKSRYKSWGSEPKSCDKTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK.
```

BRIEF DESCRIPTION OF THE DRAWINGS

FIG. 2D is a protein gel image of recombinant PBT-Fc (pointed by arrows) in its monomeric form under reducing condition (R), and in its dimeric form under normal non-reducing condition (NR).

FIG. 8A shows the $^{99m}$Tc signal of PBT-Fc is concentrated in the kidney, and there are low levels of signal accumulation in the liver and the bladder. FIG. 8B illustrates the section view showing localization of PBT-Fc to the kidney cortex, the renal parenchyma of filtration and proximal tubular reabsorption.

DEFINITIONS

Figure 1:
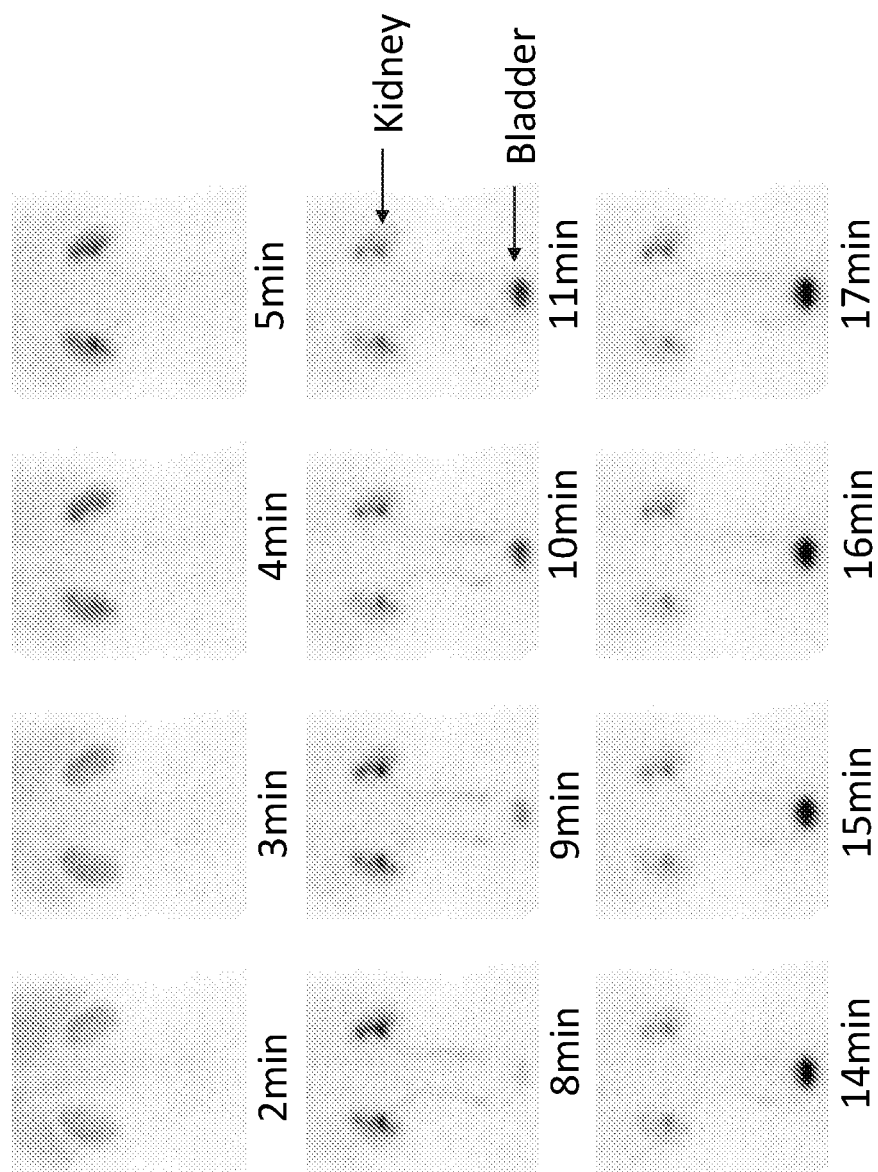
FIG. 1 is a low-resolution renogram of a patient using conventional radionuclide-bound tracer $^{99m}$Tc DTPA with renal scintigraphy.

Although any methods and materials similar or equivalent to those described herein can be used in the practice or testing of embodiments described herein, example methods, compositions, devices, and materials are described herein. However, before the present materials and methods are described, it is to be understood that this disclosure is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art. However, in case of conflict, the present specification, including definitions, will control. Accordingly, in the context of the embodiments described herein, the following definitions apply.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, pentafluorophenylalanine ("Z"), azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg"). Unnatural reactive amino acids are described in, for example, Boutureira, O. and G. J. Bernardes (2015). "Advances in chemical protein modification." Chem Rev 115(5): 2174-2195; herein incorporated by reference in its entirety.

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone. Amino acid analogs may include amino acids with various protecting groups (Isidro-Llobet, A, et al. (2009). "Amino Acid-Protecting Groups." Chemical Reviews 109(6): 2455-2504; herein incorporated by reference in its entirety).

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 30 amino acids), whereas the term "polypeptide" typically refers to longer amino acid polymers (e.g., chains having more than 30 amino acids).

As used herein, the term "artificial" refers to compositions and systems that are designed or prepared by man and are not naturally occurring. For example, an artificial peptide, peptoid, or nucleic acid is one including a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); praline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, praline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same 20 amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any peptide/polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

DETAILED DESCRIPTION

Imaging Agents

Molecular imaging agents (e.g., renal probes) including a detectable moiety, a chelation moiety, and a carrier moiety are provided. In some embodiments, methods are provided in which the molecular imaging agents described herein may be administered to a subject, the subject subsequently undergoes molecular imaging, and characteristics of the subject and/or the molecular imaging agent within the subject (e.g., intensity, distribution, change over time, etc.) are detected/monitored/characterized. Using the molecular imaging agents described herein enables imaging (e.g., PET, SPECT, etc.) for an extended period of time to develop high-resolution images of the kidney.

As used herein, the term "detectable moiety", means any entity which, when part of a molecule, allows visualization of the molecule by using molecular imaging techniques. In the context of the present disclosure, detectable moieties are entities that are detectable by molecular imaging techniques such as magnetic resonance imaging (MRI), planar scintigraphy (PS), positron emission tomography (PET), single photon emission computed tomography (SPECT), computed tomography (CT), or any combination of these techniques. In one embodiment, detectable moieties are stable, non-toxic entities.

In certain embodiments, a molecular imaging agent is detectable by a nuclear medicine molecular imaging techniques such as planar scintigraphy (PS), Positron Emission Tomography (PET) and Single Photon Emission Computed Tomography (SPECT).

SPECT and PET acquire information on the concentration of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver, whole body, etc.). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Planar scintigraphy (PS) is similar to SPECT in that it uses the same radionuclides. However, PS only generates 2D-information.

In certain embodiments, a detectable moiety in the molecular imaging agent is a radionuclide detectable by PET (e.g., Gallium-68 ($^{68}$Ga)). In other embodiments, the detectable moiety is a radionuclide detectable by planar scintigraphy or SPECT. Examples of such radionuclides include technetium-99m ($^{99m}$Tc), gallium-67 ($^{67}$Ga), yttrium-91 ($^{91}$Y), indium-111 ($^{111}$In) rhenium-186 ($^{186}$Re) and thallium-201 ($^{201}$Tl). In some embodiments, the detectable moiety is technetium-99m ($^{99m}$Tc).

In certain embodiments, the molecular imaging agent is designed to be detectable by magnetic resonance imaging (MM). MRI has the advantage of not relying on ionizing radiation. Thus, in certain embodiments, the molecular imaging agent may include a paramagnetic metal ion. An example of a paramagnetic metal ion detectable by MM is gadolinium III ($Gd^{3+}$), which is an FDA-approved contrast agent for MRI, or iron oxide, which gives a sensitive negative signal in MRI.

Chelating Agents

In some embodiments, the molecular imaging agent further includes a chelation moiety (e.g., for the complexation of paramagnetic metal ions or radionuclides). Examples of suitable chelation moieties include, but are not limited to, dimercaprol; ethylenediaminetetraacetic acid (EDTA); EDTA analogs (such as those described in US 2002/0182227 and incorporated herein by reference in its entirety); DOTA (1,4,7,10-tetraazacyclododecane-N,N',N''',N''''-tetraacetic acid); chelators described in, for example, U.S. Pat. Nos. 4,885,363; 5,087,440; 5,155,215; 5,188,816; 5,219,553; 5,262,532; and 5,358,704; and D. Meyer et al., Invest. Radiol. 1990, 25: S53-55 (herein incorporated by reference in their entireties); DTPA-bis(amide) derivatives (U.S. Pat. No. 4,687,659; herein incorporated by reference in its entirety); 2,3-Dimercapto-1-propanesulfonic acid (DMPS), dimercaptosuccinic acid (DMSA), α-Hydroxytropolones (WO 2007065007; herein incorporated by reference in its entirety), penicillamine, deferoxamine, deferasirox, chelation moieties that incorporate electron donating atoms such as O, S, P or N as Lewis bases to bind the metal (Engelstad and Wolf, "Contrast Agents", in Magnetic Resonance Imaging, Stark and Bradley, Mosby, St. Louis, 1988, pp. 161-181; herein incorporated by reference in its entirety); NOTA (1,4,7-triaza-cyclononane N,N',N"-triacetic acid); HYNIC (6-Hydrazinopyridine-3-carboxylic acid); etc. In other embodiments, the chelation moiety is obtained from other metal binding constructs (See, e.g., Carter et al. Chem. Rev. 2014, 114, 4564-4601; Que et al. Chem Rev. 2008 May; 108(5): 1517-49; Hyman and Franz. Coordination Chemistry Reviews 256 (2012) 2333-2356; herein incorporated by reference in their entireties). In one embodiment of the molecular imaging agent the chelation moiety is HYNIC. The chelator may interact with the detectable label by direct linkage or non-covalent interaction.

Carrier Moiety

The molecular imaging agent may further include a carrier moiety that is a protein carrier. In some embodiments, the carrier moiety is linked to the chelation moiety. In some embodiments, a carrier moiety is a recombinant peptide that is a fusion of two or more peptide/polypeptide elements.

Purification Tag

The carrier moiety may include a purification tag (e.g., $His_6$ (HHHHHH; SEQ ID NO: 3)), a polybasic sequence, a stabilization segment, or combinations thereof.

Of course, any N-terminal tag useful for purification of the carrier moiety may be used as part of the carrier moiety. Further, after a purification step, the purification tag may optionally be removed enzymatically or otherwise by any means. The N-terminal tag for example may be a SUMO tag, a FLAG (octapeptide), a TRx (thioredoxin), a TAP (tandem affinity purification tag), a Lucy tag (fluorescent protein), and the like. Any appropriate cleavable N-terminal tag may also be operatively or covalently linked to the carrier moiety. In addition, a suitable C-terminal protein tag may aid in the purification or expression of the carrier moiety. Further, after a purification step, the C-terminal tag may be removed enzymatically or otherwise by any means. For example, suitable C-terminal tags may include, a maltose binding protein, calmodulin binding peptide, his-patch thiofusion, tap affinity purification, epitope tags, reporter tags such as alkaline phosphatase, modified haloalkane dehalogenase, SUMO, serine proteinase such as subtilisin, post-synaptic density protein, streptavidin/biotin-based tags, chitin binding domain tag, GST tags, and polyhistidine.

Advantageously, it is not necessary to remove the purification tag from the carrier moiety prior to use of the carrier moiety.

Polybasic Tag (PBT)

The polybasic sequence (or polybasic tag (PBT) may include 6 or more consecutive amino acids (e.g., 6, 7, 8, 9, 10, 11, 12, 13, 14, 15, 16, 17, 18, 19, 20, 22, 24, 26, 28, 30, 35, 40, 50, 60, 70, 80, 90, 100, or ranges therebetween (e.g., 20-50)) having at least 25% (e.g., 25%, 30%, 35%, 40%, 45%, 50%, 55%, 60%, 65%, 70%, 75%, 80%, 85%, 90%, 95%, 100%, or ranges therebetween) basic residues (e.g., His (H), Lys (K), and Arg (R)). In some embodiments, the polybasic sequence includes the polybasic sequence of human VEGFA (e.g., SEQ ID NO: 1). In other embodiments, the polybasic sequence is amino acids 131-163 (RPKKDRARQEKKSVRGKGKGQKRKRKKSRYKSW SEQ ID NO: 3) of human VEGFA, or a variant thereof (e.g., sequence identity>70%, >75%, >80%, >85%, >90%, >95%)

Stabilization Segment

The stabilization segment may include all or a portion of the fragment crystalizable (Fc) region of an antibody (e.g., human or animal antibody). In some embodiments, the stabilization segment includes all or a portion of a human Fc region. In other embodiments, the stabilization segment includes all or a portion of the Fc region of human IgG (immunoglobulin G), for example IgG1, IgG2, IgG3, or IgG4, IgE (immunoglobulin E), IgA (immunoglobulin A) (e.g., IgA1, IgA2), IgD (immunoglobulin D), or IgM (immunoglobulin M). In some embodiments, the stabilization segment may include all or a portion of Fc region of human IgG1. In other embodiments, the stabilization segment includes all or a portion of bovine serum albumin (BSA) or human serum albumin (HSA) or any other protein fragment or molecule that, in combination with a PBT, is capable of being locked in a cellular membrane of the kidney. In some embodiment, the stabilization segment may include an Fc fragment as exemplified by SEQ ID NO: 2.

In some embodiments, a carrier moiety includes a purification tag (e.g., His6), a polybasic sequence, and a stabilization segment (e.g., Fc). In some embodiments, the purification tag is enzymatically removed and the carrier moiety comprises a polybasic sequence and a stabilization segment. In some embodiments, the carrier moiety includes an N-terminal $His_6$ tag (e.g., for purification), followed by, from the N- to C-termini, the PBT (polybasic tag or sequence) from the human VEGFA sequence (amino acids 131-163), and Fc of human IgG1 (stabilization segment). The carrier moiety may be any amino acids in length. The carrier moiety must may be a recombinant protein that must include PBT and stabilization segment. The carrier moiety may include additional spacer amino acids between, for example, the purification tag and the polybasic tag or between the polybasic tag and the stabilization segment. Further, additional amino acids may be present C-terminally to the stabilization segment of the carrier moiety. An exemplary carrier moiety includes an N-terminal $His_6$ tag (SEQ ID NO; 3, e.g., for purification), followed by, from the N- to C-termini, the PBT (polybasic tag or sequence) OF SEQ ID NO: 1 from the human VEGFA sequence (amino acids 131-163), and a Fc of human IgG1 (SEQ ID NO: 2, stabilization segment). An exemplary carrier moiety comprises SEQ ID NO: 4. An exemplary carrier moiety includes an N-terminal $His_6$ tag (e.g., for purification), followed by, from the N- to C-termini, the PBT (polybasic tag or sequence) from the human VEGFA sequence (amino acids 131-163), and a Fc of human IgG1 (stabilization segment), as expressed in E. coli. strain BL21DE3 and purified by Ni-NTA chromatography (the "PBT-Fc carrier moiety"). 20 μg of the PBT-Fc carrier moiety may then be labeled with HYNIC (6-Hydrazinopyridine-3-carboxylic acid) following a standard labeling protocol.

In some embodiments, the carrier moiety includes one or more unnatural amino acids, amino acid analogs, etc., as defined above. In some embodiments, the carrier moiety comprises a polybasic tag operatively linked to a stabilization segment by standard recombinant nucleic acid methodologies. Provided these two elements are present, any methods of combining or forming a carrier moiety that comprises both a PBT and stabilization segment are encompassed by the present invention.

Linkage of Carrier Moiety and Chelation Moiety

In some embodiments, the chelation moiety and the carrier moiety are directly attached, or covalently linked. In some embodiments, a chelation moiety and carrier moiety are indirectly attached by a linker. A linker may be any suitable chemical moiety capable of linking, connecting, or tethering the chelation moiety to the carrier moiety. In some embodiments, the linker is a polymer of one or more repeating or non-repeating monomer units (e.g., nucleic acid, amino acid, carbon-containing polymer, carbon chain, etc.). A wide variety of linkers may be used. In some embodiments, the linker includes a linear or branched, cyclic or heterocyclic, saturated or unsaturated, structure having 1-20 nonhydrogen atoms (e.g., C, N, P, O and S) and is composed of any combination of alkyl, ether, thioether, imine, carboxylic, amine, ester, carboxamide, sulfonamide, hydrazide bonds and aromatic or heteroaromatic bonds. In some embodiments, linkers are longer than 20 nonhydrogen atoms (e.g. 21 non-hydrogen atoms, 25 non-hydrogen atoms, 30 non-hydrogen atoms, 40 non-hydrogen atoms, 50 non-hydrogen atoms, 100 non-hydrogen atoms, etc.)

In other embodiments, the linker includes 1-50 non-hydrogen atoms (in addition to hydrogen atoms) selected from the group of C, N, P, O and S (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 non-hydrogen atoms). The scope of embodiments herein is not limited by the types of linkers available, and embodiments are not limited to any particular linker group. A variety of linker groups are contemplated, and suitable linkers could include, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, the linker is cleavable (e.g., enzymatically) (e.g., TEV protease site), chemically, photoinduced, etc.

In some embodiments, the chelation moiety and carrier moiety (or a linker and a chelation moiety, or linker and a carrier moiety, etc.) are linked by any suitable chemistry. Chemistries for attaching a moiety, such as chelation moiety, to a carrier moiety are well established. Exemplary chemistries for such attachment include native chemical ligation; Staudinger ligation; "traceless" Staudinger ligation; amide coupling; methods that employ activated esters, methods that target lysine, tyrosine and/or cysteine residues; imine bond formation (with and without ortho-boronic acid); boronic acid/diol interactions; disulfide bond formation; copper/copper free azide, diazo, and tetrazine "click" chemistry; UV promoted thiolene conjugation; diazirine photolabeling; Diels-Alder cycloaddition; metathesis reaction; Suzuki cross-coupling; thiazolidine (Step-4) coupling; streptavidin/biotin complementation; etc. In some cases the stoichiometry of chelation moiety to carrier moiety is 1:1. In some cases the stoichiometry of chelation moiety to carrier moiety is 2:1, 3:1, 5:1 or greater.

Label-Chelant-Carrier Uses

In some embodiments, a molecular imaging agent described herein is administered to a subject. Embodiments herein are not limited by the route of administration. Exemplary routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, following administration of a molecular imaging agent described herein to a subject, all or a portion (e.g., kidneys) of the subject is imaged to assess one or more characteristics (e.g., structural characteristic, function, etc.) of the subject (e.g., kidney of the subject) and/or the localization of the molecular imaging agent.

In some embodiments, the subject undergoes a whole body scan. In some embodiments, the subject undergoes a renal scan. In some embodiments, a renal scan (e.g., renal scintigraphy, renogram/renography, etc.) is a nuclear medicine exam in which a small amount of radioactive material (radioisotope) is used to measure the function of the kidneys. In some embodiments, imaging is performed by any suitable modality that allows for non-invasive detection, monitoring, localization, and/or imaging of the molecular imaging agent following administration to the subject. In some embodiments, the particular modality is selected based on the molecular imaging agent. In some embodiments, the particular molecular imaging agent is selected based on the imaging modality. Examples of imaging modalities that may be suitably and selectively used include X-ray systems, ultrasound (UT) systems, magnetic resonance imaging (MRI) systems, computed tomography (CT) systems, single photon emission computed tomography (SPECT), positron emission tomography (PET) systems, etc. In particular embodiments, SPECT or PET are used for renal scan.

In some embodiments, a medical imaging system for use with embodiments herein may include any device capable of generating digital data representing an anatomical region of interest (e.g., kidney). Image data representative of one or more images may be communicated between the medical imaging system and a processor unit. Medical imaging systems and the processor unit may utilize wired communication and/or wireless communication. Processor unit may include any type of computing device, computational circuit, or any type of processor or processing circuit capable of executing a series of instructions that are stored in a memory (not shown) associated with the processor unit. Processor unit 26 may be adapted to run an operating system platform and application programs. Processor unit may receive user inputs from any suitable device. In some embodiments, data collected from imaging scans is generated, processed, and/or displayed using techniques understood in the field.

In some embodiments, the methods described herein are performed in conjunction with a renal function test. Examples of such tests include measurement of: blood urea nitrogen (BUN) test, serum creatinine, creatinine clearance rate, etc.

In some embodiments, the methods described herein are performed to assess renal function is a subject. Such scans may be used to evaluate one or more of decreased blood flow to the kidneys, renovascular hypertension, tumors or cysts, abscesses, kidney disease, the success of kidney treatments, the rejection of a kidney transplant, etc.

In some embodiments, prior to administration of a molecular imaging agent described herein, a subject is administered diuretics, or water pills, ACE inhibitors, beta blockers, nonsteroidal anti-inflammatory drugs (NSAIDs), etc.

Experiments

Experiments were conducted in rats and mice using a molecular imaging agent including $^{99m}$Tc as the detection moiety, HYNIC as the chelation moiety, and PBT-Fc as the carrier moiety. In one example, the molecular imaging agent was prepared using the following method:

1. Prepare the PBT-Fc in phosphate-buffered saline (PBS, pH8-8.5) at 1 mg/ml.
2. Dissolve the HYNIC in DMF (Dimethylformamide) to a final concentration of 9 mg/ml.
3. Add 10 μl HYNIC solution to 0.5 ml of the PBT-Fc solution (pH 8-8.5). Incubate for 1 hr at room temperature with gentle agitation.
4. At the same time, equilibrate 1 desalting column with a citrate buffer solution (20 mM citrate, 100 mM NaCl, pH 5.2), 4 times (1000 g, 4 min each).
5. After HYNIC labeling, desalt the HYNIC/PBT-Fc mixture using the column to remove free HYNIC and to exchange to a citrate buffer, pH 5.2.
6. Dissolve tricine in a citrate buffer solution (pH 5.2) to a concentration of 100 mg/ml.
7. Add 15 μl of the tricine solution to a 100 μl aliquot of the HYNIC-labeled PBT-Fc.
8. Prepare a stannous chloride solution to a concentration of 10 mg/ml in 0.1N HCl.
9. Add $^{99\text{-}m}$Tc pertechnetate to (6), invert to mix.
10. Immediately add 4 μl of the stannous chloride solution to (9), invert to mix. Incubate for 1 hr at room temperature.
11. At the same time, equilibrate 1 desalting column with PBS or saline (4 times, 1000 g, 4 min each).
12. After 1 hr, desalt the $^{99\text{-}m}$Tc/HYNIC/PBT-Fc mixture and measure radioactivity of the flow-through ($^{99\text{-}m}$Tc/HYNIC/PBT-Fc molecular imaging agent) and column (free $^{99m}$Tc).
13. For injecting rats, 300 MBq of total radioactivity of the $^{99\text{-}m}$Tc/HYNIC/PBT-Fc molecular imaging agent is injected via the tail vein.
14. For injecting mouse, 37 MBq of total radioactivity of the $^{99\text{-}m}$Tc/HYNIC/PBT-Fc molecular imaging agent is injected via the tail vein.
15. For the molecular imaging agent-directed SPECT scanning of mice, 45 min after the injection of the $^{99\text{-}m}$Tc/HYNIC/PBT-Fc molecular imaging agent, the animals were scanned in a micro-SPECT (model U-SPECT$^+$/CT manufactured by MILabs) for 15 minutes.

Upon administration of the molecular imaging agent to the test subjects, it was observed to be filtered by the test subjects' glomerulus and then fixed (e.g., permanently) at the basement membrane of the downstream renal tubules without being further excreted into urine. That is, following the initial kidney perfusion—it was observed that during the glomerular filtration phase of the molecular imaging agent, during which the kidney clears $^{99m}$Tc (the detection moiety) from blood circulation—the radio signals accumulated in the kidney reach the plateau after 10-20 minutes (considering that the natural decay of $^{99m}$Tc is negligible). During the next stationary phase, the imaging (e.g., by SPECT camera) collects signals of the kidney for an extended period of time. Consequently, high-resolution imaging (e.g., 3-dimensional radio images) that reflect kidney filtration patterns are obtained.

As shown in FIG. 1, using conventional radionuclide-bound tracers, such as:

$^{99m}$Tc Diethylenetriamine-Pentaacetic Acid ($^{99m}$Tc DTPA)

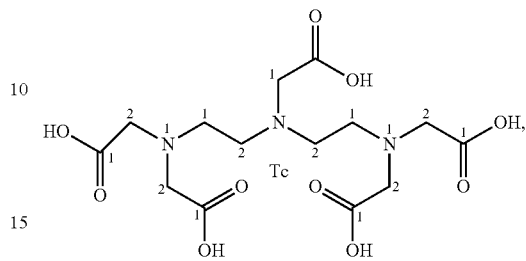

and $^{99m}$Tc Mercaptoacetyltriglycine ($^{99m}$Tc MAG3) (Shown Below)

Figure 7:
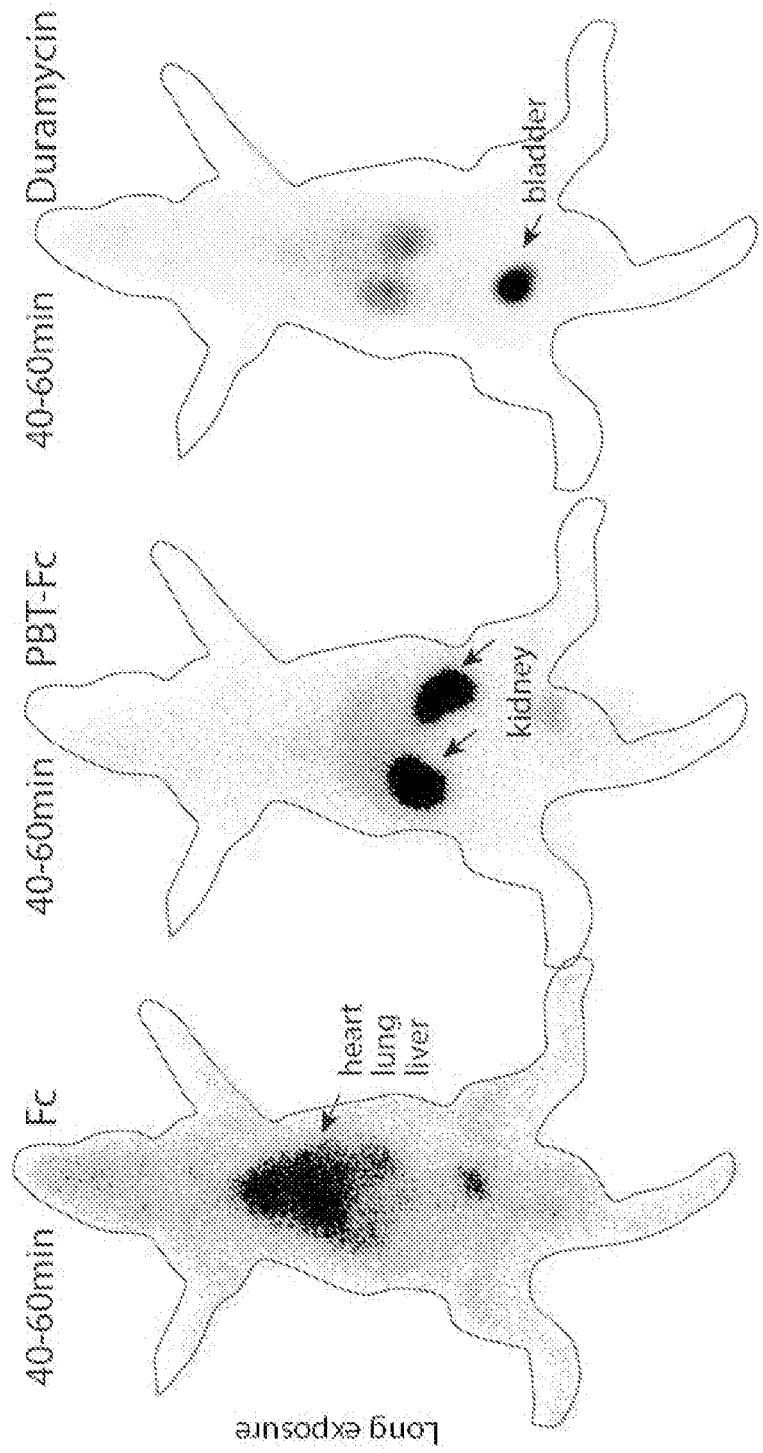
FIG. 7 are steady state (from 40 to 60 min) distribution patterns of Fc, PBT-Fc and Duramycin (Dur) in rats shown with images obtained from continuous signal acquisition between 40 and 60 min after the injection of the tracers.

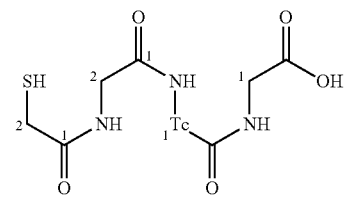

the tracer is shown to filter through the kidney and into the bladder within a matter of less than 20 minutes. However, using the molecular imaging agent described, an example $^{99m}$TC/HYNIC/PBT-Fc, shown below, the agent is concentrated in the kidney without being excreted into urine (FIG. 7). Also, as can be seen in FIG. 2, using conventional and PBT-Fc-based renal scintigraphy, it was clear that the traditional tracer, DTPA, entered the subject and "washed out" of the system within 20 minutes. The PBT-Fc agent, however, stayed in the subject's system long enough for steady state high resolution images to be acquired (for example 60 minutes in FIG. 7).

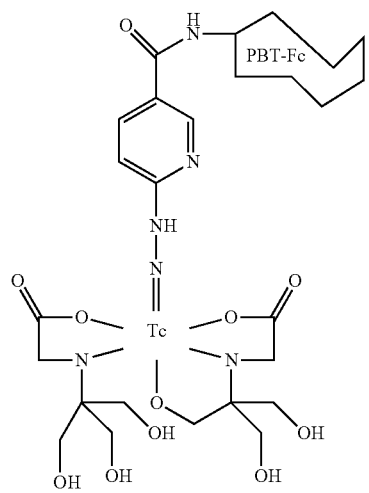

Example $^{99m}$Tc/HYNIC/PBT-Fc Molecular Imaging Agent

Consequently, the steady state nuclear image from $^{99m}$Tc/HYNIC/PBT-Fc molecular imaging agent permits imaging (e.g., planar scintigraphy, PET, SPECT, etc.) for an extended period of time to develop high-resolution images of the kidney. Using an experimental unilateral ischemia-reperfusion injury model of the kidney, the new molecular imaging agent captured the severity of the lesions with a spatial context.

Figure 2D:
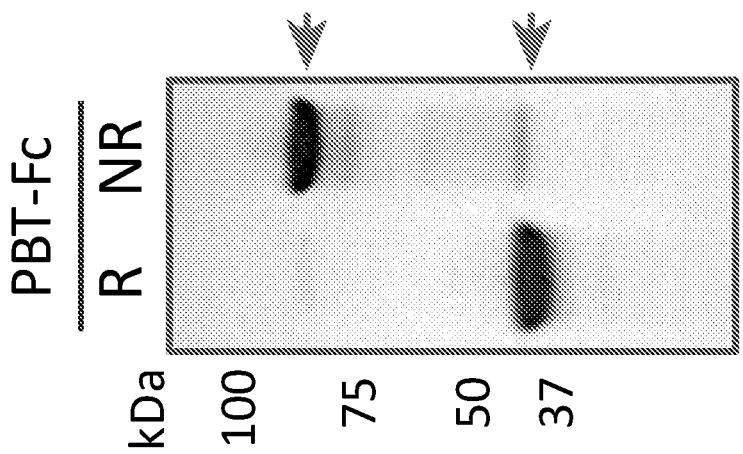
FIG. 2A-D are graphical representations of three carriers that may be used to make molecular imaging agents, including recombinant Fc (the stabilization segment)(FIG. 2A); recombinant PBT-Fc fusion protein (FIG. 2B), and polypeptide carrier Duramycin as a control (FIG. 2C).
Figure 2A:
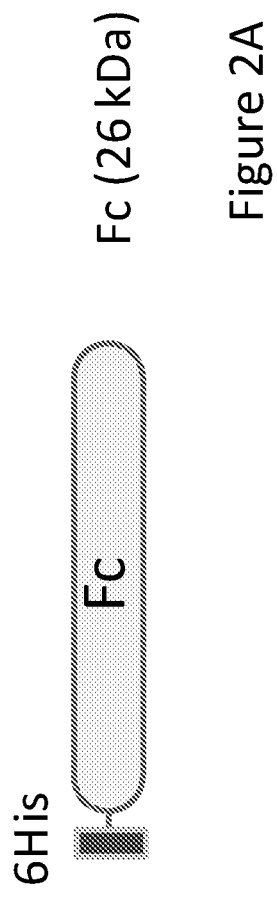
Figure 2B:
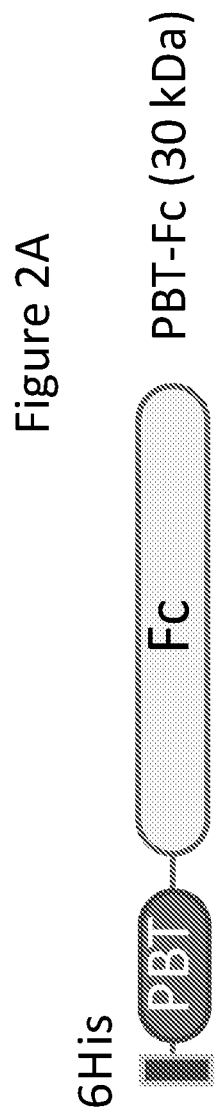
Figure 2C:
Figure 3:
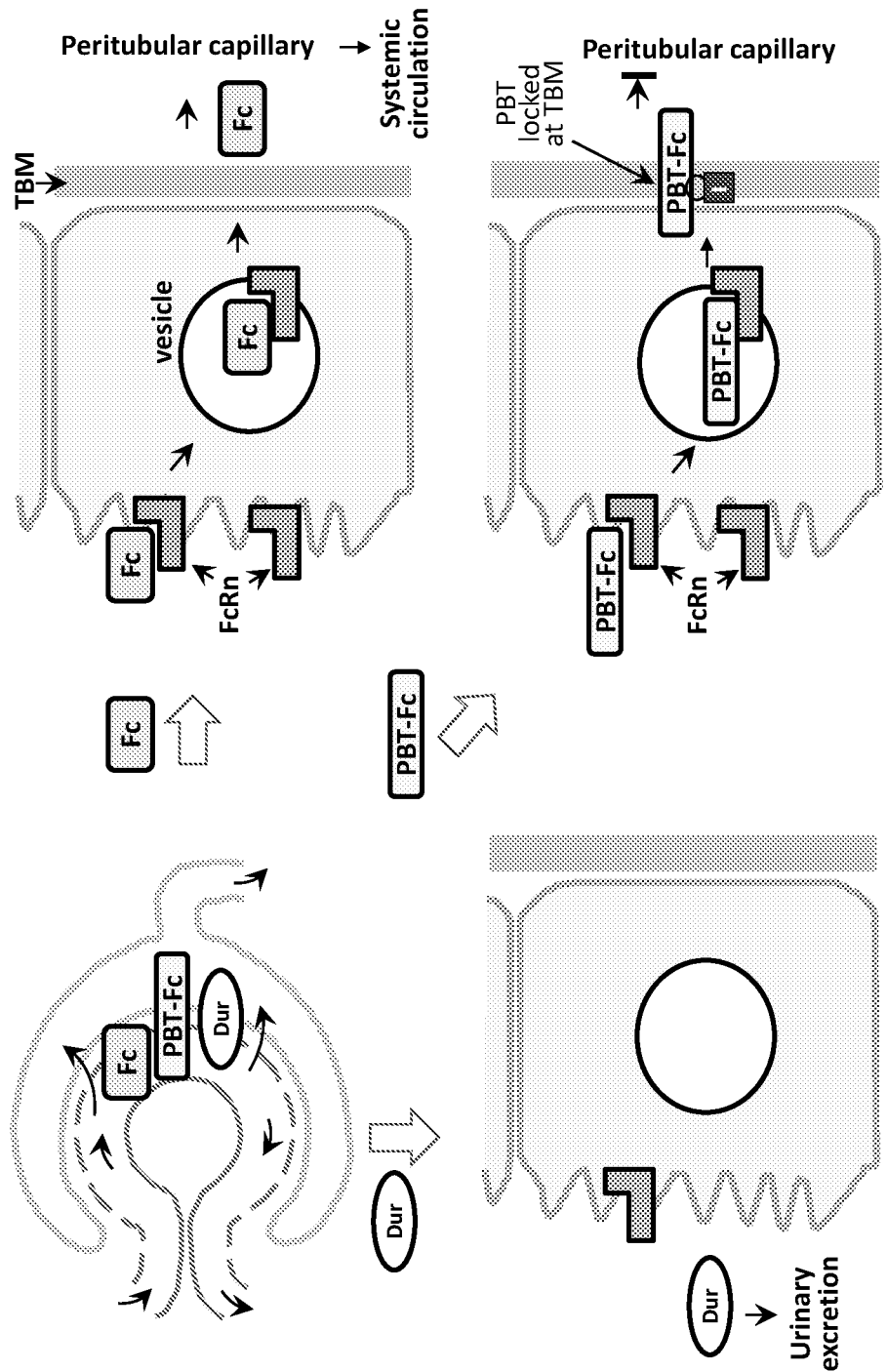
FIG. 3 is a schematic model of the movement of PBT-Fc, Fc-alone, and Duramycin through the glomerulus and the renal tubular epithelial cells.
Figure 4:
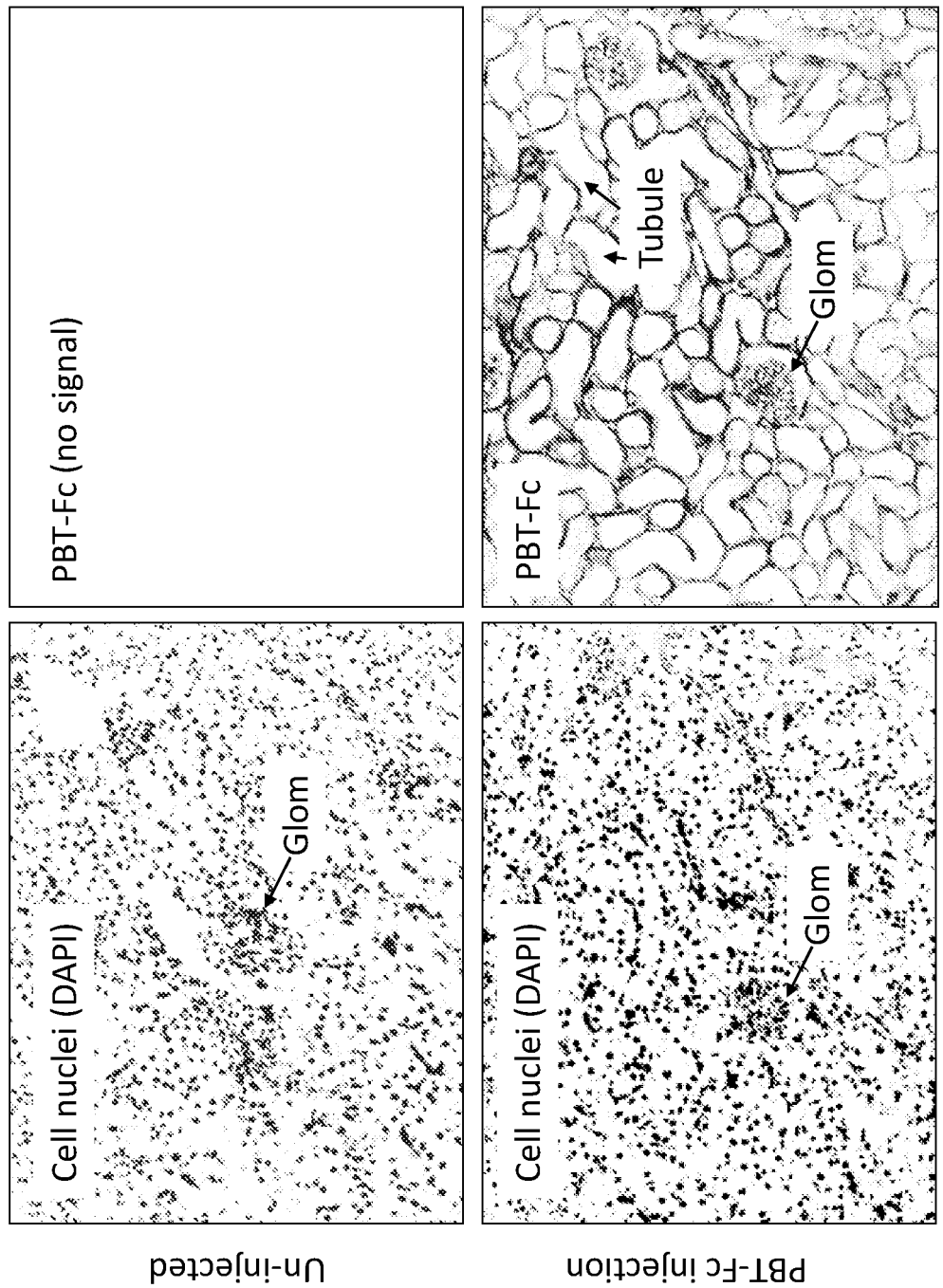
FIG. 4 illustrates the renal histology of the PBT-Fc carrier moiety (in immunofluorescence, or IF) with (bottom) or without (top) the injection of the probe to mice, showing the distribution of the probe mainly in the tubular basement membrane.
Figure 5:
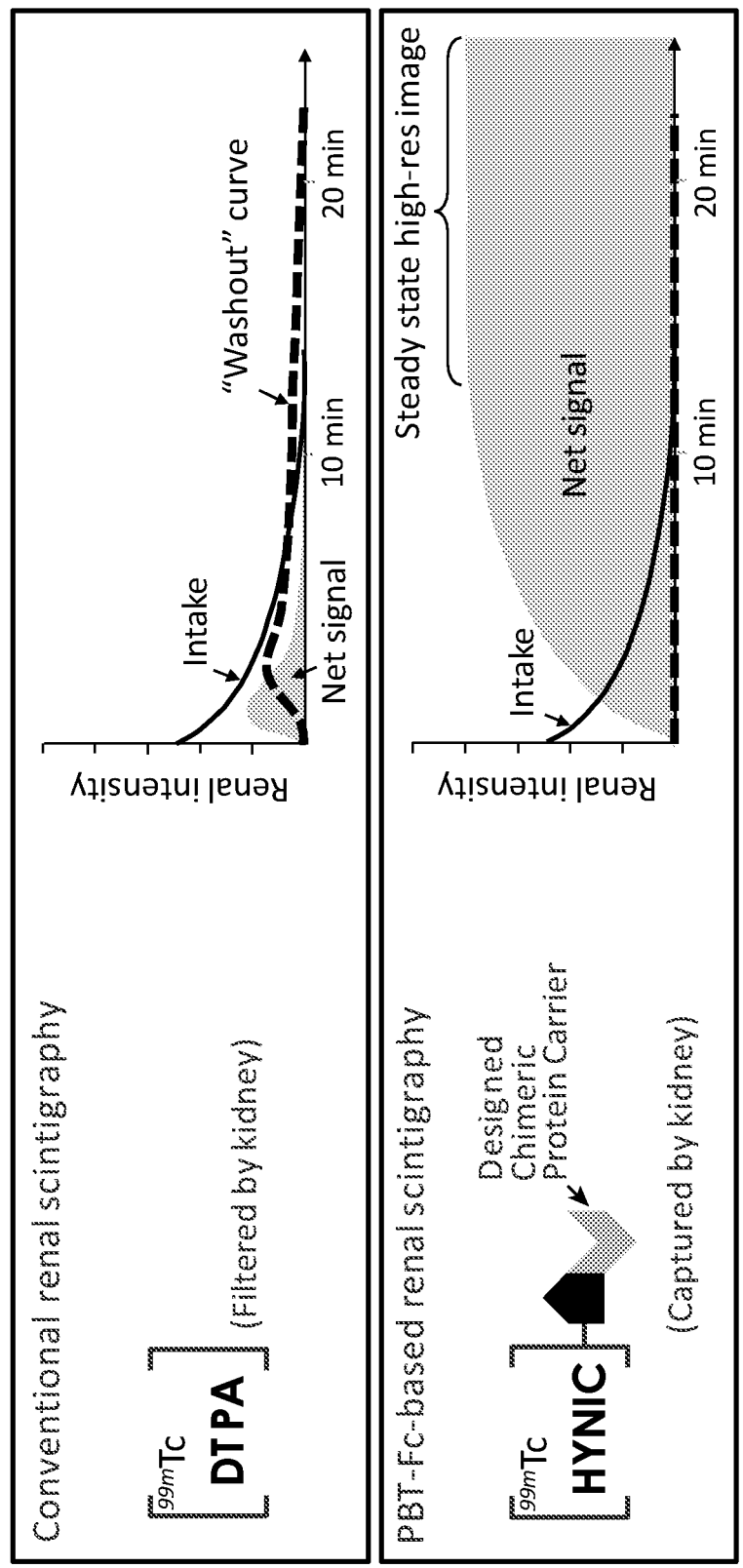
FIG. 5 is a schematic comparison of conventional renal scintigraphy versus the new PBT-Fc-directed renal scintigraphy. PBT-Fc is retained by the kidney with no urinary excretion (no washout) and the net tracer signals accumulate to a high steady-stage level that improves radio signal acquisition by the gamma camera.

In order to more closely compare the results of the molecular imaging agent in the subjects, three imaging agents were produced using $^{99m}$Tc as the detection moiety, HYNIC as the chelation moiety, and 1) Fc alone, 2) PBT-Fc (as detailed above), and 3) duramycin as the carrier moiety, as shown in FIGS. 2A, 2B, and 2C, respectively. As shown in FIG. 4, it was found that the Fc binds the FcRn on the surface of renal tubular epithelial cells, while the Duramycin is excreted through urination. It was then found that the complexes then undergo transcytosis before PBT-Fc is released to the basal side of the epithelium. Unlike Fc-alone, or more traditional tracer agents, which reenters blood circulation via peritubular capillaries, PBT-Fc is "trapped" in the tubular basement membrane (TBM) (See also FIG. 3).

Figure 6:
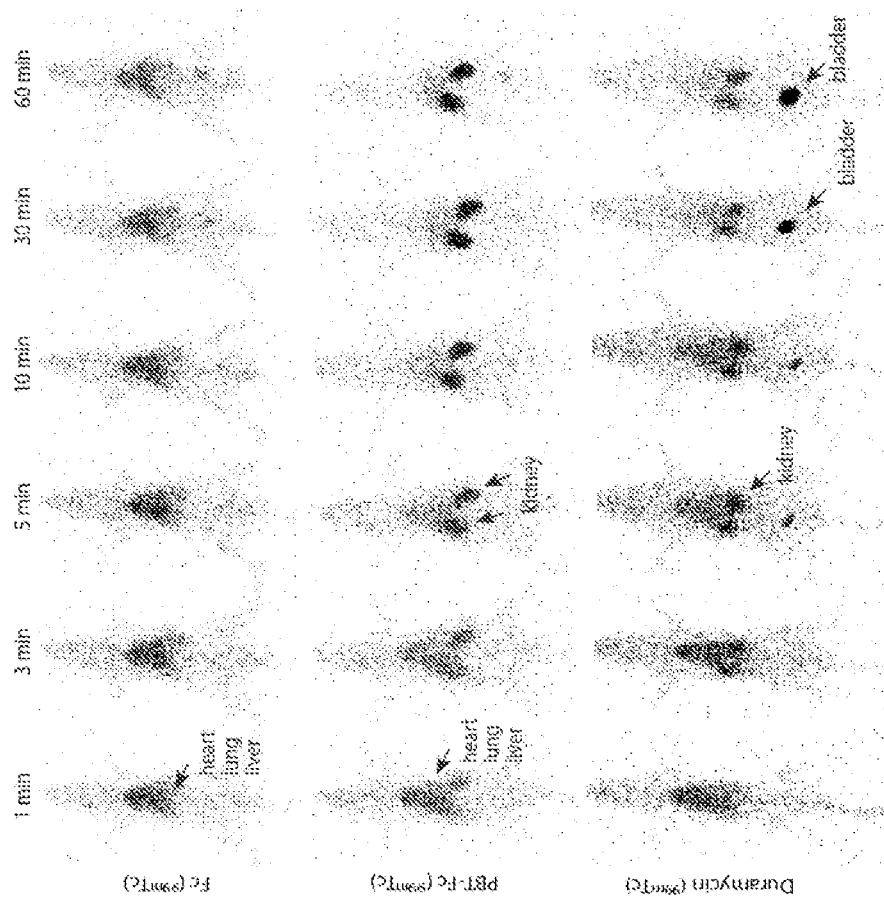
FIG. 6 is are a compilation of real time planar scintigraphy images of Fc, PBT-Fc and Duramycin carriers, showing distinct dynamics of redistribution patterns in rats.
Figures 8A, 8B:
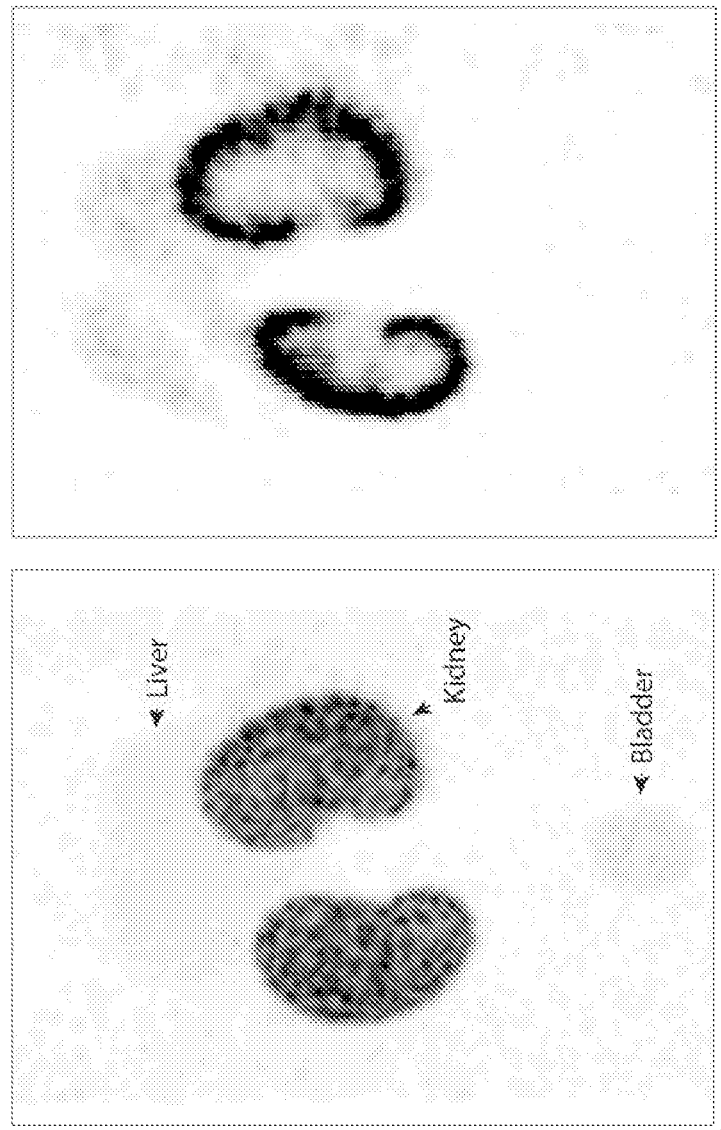
FIGS. 8A and 8B are steady state (from 45 min onward) PBT-Fc carrier moiety signals are concentrated in mouse kidney.
Figures 9A, 9B:
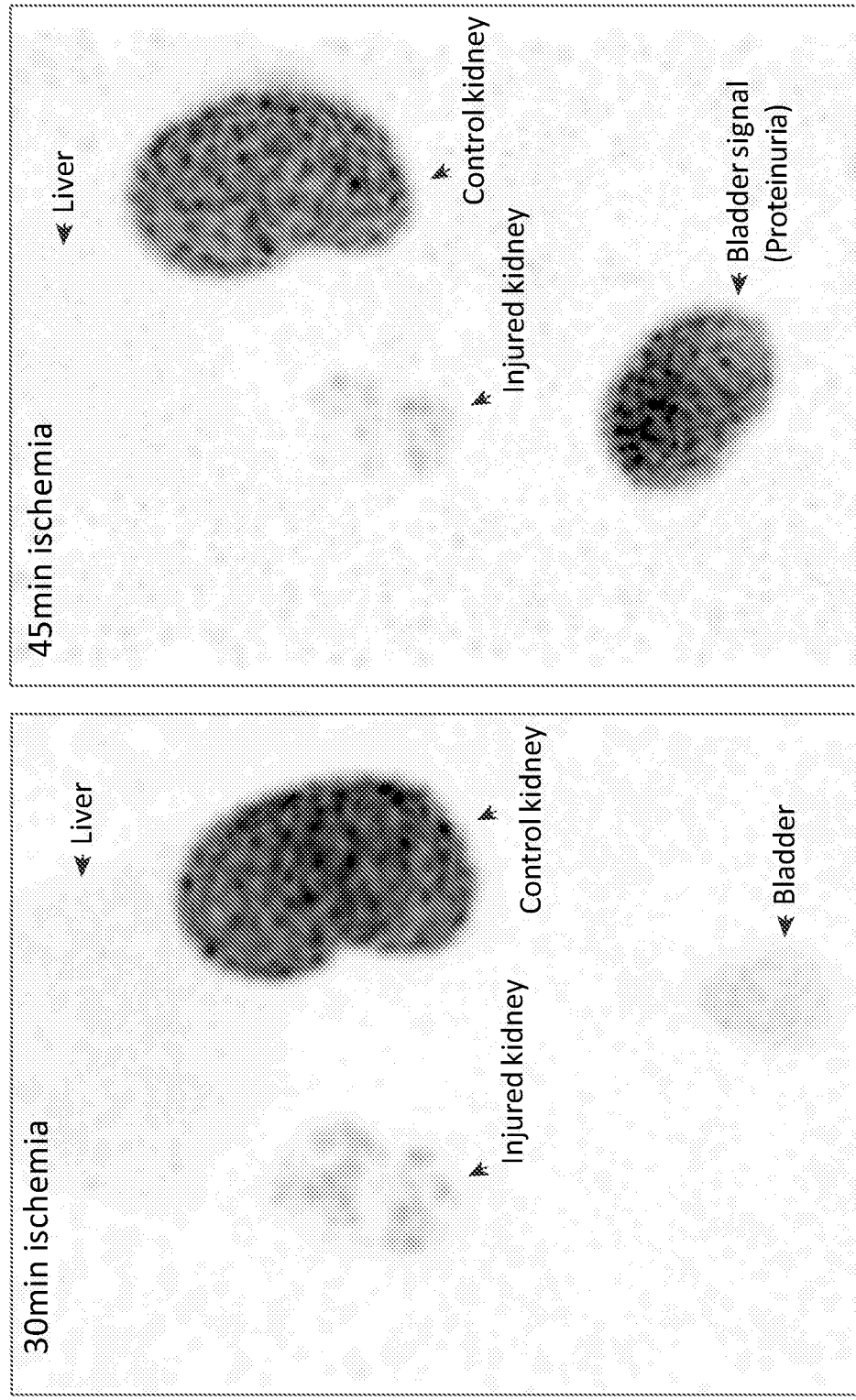
FIGS. 9A and 9B are SPECT scans of mice, showing unilateral kidney injury (ischemia-reperfusion injury (IRI) model of mouse) using PBT-Fc-based carrier-based agents. The kidney with more severe kidney injury (45 min ischemia) (FIG. 9B) also shows bladder signal indicative of proteinuria.
Figures 10A, 10B:
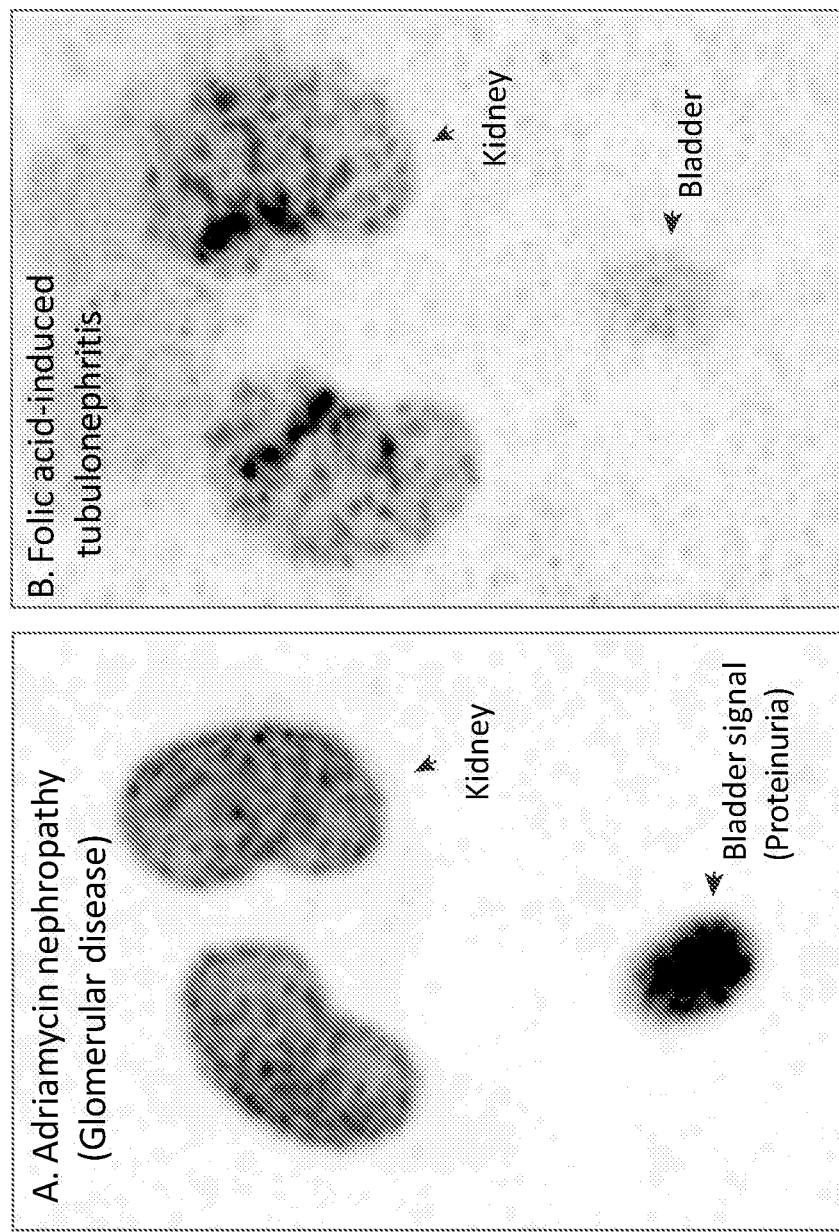
FIGS. 10A and 10B are Fc-PBT-directed SPECT steady state images (3-dimensional composite) of mice showing distinct patterns of renal injury types caused by nephrotoxic drugs. (A) SPECT images of kidney glomerular disease of Adriamycin/Doxorubicin nephropathy and (B) acute tubular injury with folic acid.

FIGS. 6 and 7 further illustrate the ability of the $^{99m}$Tc/HYNIC/PBT-Fc agent to accumulate and remain the kidneys of the subjects for much longer than that of the Fc-alone and Duramycin agents. FIGS. 8, 9, and 10 also illustrate the accumulation and fixation of the $^{99m}$Tc/HYNIC/PBT-Fc agent in the kidneys of the test subjects and the ability of the viewer to more clearly distinguish healthy versus damages kidneys and use the rate of filtration to access kidney function, or lack thereof.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

The invention claimed is:

1. A molecular imaging agent comprising a detectable moiety, a chelation moiety, and a carrier moiety, wherein the detectable moiety is coupled to the chelation moiety, wherein the chelation moiety is linked to the carrier moiety, wherein the carrier moiety comprises a purification tag, a polybasic sequence that comprises at least 70% sequence identity with SEQ ID NO: 1, and a human Fc sequence.

2. The molecular imaging agent of claim 1, wherein the detectable moiety comprises $^{99m}$Tc, $^{68}$Ga, $^{67}$Ga, $^{91}$Y, $^{111}$In, $^{186}$Re, or $^{201}$Tl.

3. The molecular imaging agent of claim 1, wherein the chelation moiety comprises HYNIC.

4. The molecular imaging agent of claim 1, wherein the purification tag is a His$_6$ tag (SEQ ID NO: 3).

5. The molecular imaging agent of claim 1,
wherein the detectable moiety is $^{99m}$Tc;
wherein the chelation moiety comprises HYNIC; and
wherein the carrier moiety comprises from N-terminus to C-terminus:
a His$_6$ purification tag,
the polybasic sequence is a human polybasic sequence, and
the human Fc stabilization segment.

6. A method of assessing kidney function of a subject, wherein the method comprises:
administering to the subject a molecular imaging agent comprising a detectable moiety, a chelation moiety, and a carrier moiety, wherein the detectable moiety is coordinated by the chelation moiety, and wherein the chelation moiety is linked to the carrier moiety, wherein the carrier moiety comprises a purification tag, a polybasic sequence that comprises at least 70% sequence identity with SEQ ID NO: 1, and a human Fc sequence; and
performing a renal scan of the subject.

7. The method of claim 6, wherein upon administration of the molecular imaging agent to a subject, the molecular imaging agent is cleared from the blood by kidneys of the subject.

8. The method of claim 6, wherein less than 10% of the molecular imaging agent in the kidney of a subject is cleared to the bladder of the subject per 10 minute period.

9. The method of claim 6, wherein the detectable moiety is $^{99m}$Tc, $^{68}$Ga, $^{67}$Ga, $^{91}$Y, $^{111}$In, $^{186}$Re, or $^{201}$Tl.

10. The method of claim 6, wherein the chelation moiety is HYNIC.

11. The method of claim 6, wherein the purification tag is a His$_6$ tag (SEQ ID NO: 3).

12. The method of claim 6, wherein the renal scan comprises positron emission tomography (PET) or single photon emission computed tomography (SPECT).

* * * * *

SEQUENCE LISTING

<160> NUMBER OF SEQ ID NOS: 4

<210> SEQ ID NO 1
<211> LENGTH: 33
<212> TYPE: PRT
<213> ORGANISM: Artificial Sequence
<220> FEATURE:
<223> OTHER INFORMATION: Synthetic-Polybasic tag (PBT), amino acids
      131-163 of human VEGFA

<400> SEQUENCE: 1

Arg Pro Lys Lys Asp Arg Ala Arg Gln Glu Lys Lys Ser Val Arg Gly
1               5                   10                  15

Lys Gly Lys Gly Gln Lys Arg Lys Arg Lys Lys Ser Arg Tyr Lys Ser
            20                  25                  30

Trp

<210> SEQ ID NO 2
<211> LENGTH: 232
<212> TYPE: PRT
<213> ORGANISM: Artificial Sequence
<220> FEATURE:
<223> OTHER INFORMATION: Synthetic- FC region of human IgG1/IGHG1
      protein sequence accession: AIC63046, encoded by KJ905795.1
      transcript

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala

```
                    100                 105                 110
Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 6
<212> TYPE: PRT
<213> ORGANISM: Artificial Sequence
<220> FEATURE:
<223> OTHER INFORMATION: Synthetic- Affinity tag

<400> SEQUENCE: 3

His His His His His His
1               5

<210> SEQ ID NO 4
<211> LENGTH: 319
<212> TYPE: PRT
<213> ORGANISM: Artificial Sequence
<220> FEATURE:
<223> OTHER INFORMATION: Synthetic- Full length sequence of the PBT-Fc
      probe including the 6xHis, PBT and Fc segments in an amino
      terminus to carboxyl terminus order, and additional linkers

<400> SEQUENCE: 4

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
            35                  40                  45

Gly Ser Glu Phe Arg Pro Lys Lys Asp Arg Ala Arg Gln Glu Lys Lys
        50                  55                  60

Ser Val Arg Gly Lys Gly Lys Gly Gln Lys Arg Lys Arg Lys Lys Ser
65                  70                  75                  80

Arg Tyr Lys Ser Trp Gly Ser Glu Pro Lys Ser Cys Asp Lys Thr His
                85                  90                  95

Thr Cys Pro Pro Cys Pro Ala Pro Glu Leu Leu Gly Gly Pro Ser Val
                100                 105                 110

Phe Leu Phe Pro Pro Lys Pro Lys Asp Thr Leu Met Ile Ser Arg Thr
            115                 120                 125

Pro Glu Val Thr Cys Val Val Val Asp Val Ser His Glu Asp Pro Glu
        130                 135                 140

Val Lys Phe Asn Trp Tyr Val Asp Gly Val Glu Val His Asn Ala Lys
```

-continued

```
145                 150                 155                 160
Thr Lys Pro Arg Glu Glu Gln Tyr Asn Ser Thr Tyr Arg Val Val Ser
                165                 170                 175
Val Leu Thr Val Leu His Gln Asp Trp Leu Asn Gly Lys Glu Tyr Lys
                180                 185                 190
Cys Lys Val Ser Asn Lys Ala Leu Pro Ala Pro Ile Glu Lys Thr Ile
                195                 200                 205
Ser Lys Ala Lys Gly Gln Pro Arg Glu Pro Gln Val Tyr Thr Leu Pro
                210                 215                 220
Pro Ser Arg Asp Glu Leu Thr Lys Asn Gln Val Ser Leu Thr Cys Leu
225                 230                 235                 240
Val Lys Gly Phe Tyr Pro Ser Asp Ile Ala Val Glu Trp Glu Ser Asn
                245                 250                 255
Gly Gln Pro Glu Asn Asn Tyr Lys Thr Thr Pro Pro Val Leu Asp Ser
                260                 265                 270
Asp Gly Ser Phe Phe Leu Tyr Ser Lys Leu Thr Val Asp Lys Ser Arg
                275                 280                 285
Trp Gln Gln Gly Asn Val Phe Ser Cys Ser Val Met His Glu Ala Leu
    290                 295                 300
His Asn His Tyr Thr Gln Lys Ser Leu Ser Leu Ser Pro Gly Lys
305                 310                 315
```